(12) United States Patent
Lauten et al.

(10) Patent No.: US 8,906,409 B2
(45) Date of Patent: Dec. 9, 2014

(54) ACOUSTICALLY SENSITIVE DRUG DELIVERY PARTICLES COMPRISING NON-LAMELLAR FORMING PHOSPHATIDYLCHOLINE

(75) Inventors: Cecilia Leal Lauten, Oslo (NO); Karen Sibylla Røgnvaldsson, Olso (NO); Sigrid Fossheim, Oslo (NO); Esben A. Nilssen, Oslo (NO); Tove J. Evjen, Oslo (NO)

(73) Assignee: Epitarget AS, Oslo (DE)

( * ) Notice: Subject to any disclaimer, the term of this patent is extended or adjusted under 35 U.S.C. 154(b) by 0 days.

(21) Appl. No.: 13/376,686

(22) PCT Filed: Jun. 8, 2010

(86) PCT No.: PCT/NO2010/000216
§ 371 (c)(1),
(2), (4) Date: Feb. 1, 2012

(87) PCT Pub. No.: WO2010/143970
PCT Pub. Date: Dec. 16, 2010

(65) Prior Publication Data
US 2012/0189689 A1    Jul. 26, 2012

(30) Foreign Application Priority Data

Jun. 8, 2009  (NO) .................................. 20092195

(51) Int. Cl.
| | | |
|---|---|---|
| A61K 47/24 | (2006.01) |
| A61K 9/127 | (2006.01) |
| A61K 9/14 | (2006.01) |
| A61P 35/00 | (2006.01) |
| A61P 37/00 | (2006.01) |
| A61P 31/00 | (2006.01) |
| A61P 29/00 | (2006.01) |
| B82Y 5/00 | (2011.01) |
| A61K 9/00 | (2006.01) |
| A61K 31/704 | (2006.01) |

(52) U.S. Cl.
CPC ............. *A61K 9/0009* (2013.01); *A61K 9/0019* (2013.01); *A61K 31/704* (2013.01); *A61K 9/1272* (2013.01); *A61K 9/1271* (2013.01); *Y10S 977/773* (2013.01); *Y10S 977/906* (2013.01)
USPC ........... 424/450; 514/786; 424/400; 977/773; 977/906

(58) Field of Classification Search
USPC ......................................................... 424/450
See application file for complete search history.

(56) References Cited

U.S. PATENT DOCUMENTS

| | | | |
|---|---|---|---|
| 5,858,399 A * | 1/1999 | Lanza et al. .................. | 424/450 |
| 2002/0182258 A1* | 12/2002 | Lunsford et al. .............. | 424/499 |
| 2004/0156888 A1* | 8/2004 | Jensen et al. .................. | 424/450 |

FOREIGN PATENT DOCUMENTS

| | | | |
|---|---|---|---|
| WO | WO-2007-078060 | * | 7/2007 |
| WO | WO-2008-120998 | * | 10/2008 |

OTHER PUBLICATIONS

Lin H-Y, PEG-Lipids and oligo(ethylene glycol) surfactants enhance the ultrasonic permeabilizability of liposomes, Langmuir, 2003, 19, 1098-1105.*

* cited by examiner

*Primary Examiner* — Frederick Krass
*Assistant Examiner* — Celeste A Roney
(74) *Attorney, Agent, or Firm* — Birch, Stewart, Kolasch & Birch, LLP

(57) ABSTRACT

Novel acoustically sensitive drug carrying particles comprising non-lamellar forming lipids are disclosed, as well as uses and methods thereof. The drug carrying particles accumulate in the diseased target tissue and efficiently release their payload upon exposure to acoustic energy.

19 Claims, 10 Drawing Sheets

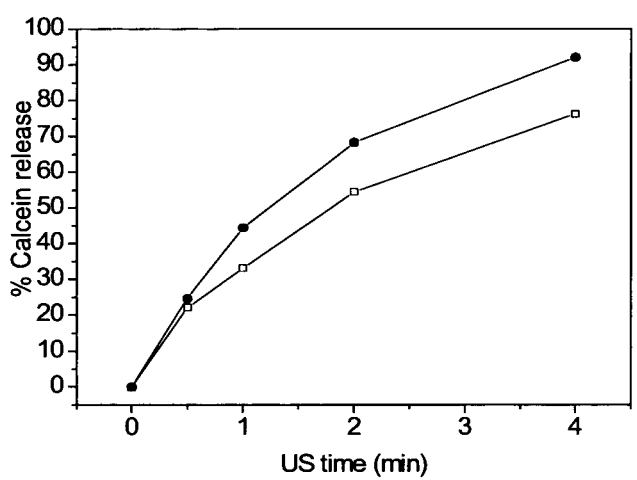
Fig. 1. Hexanol improves sonosensitivity of DSPC liposomes

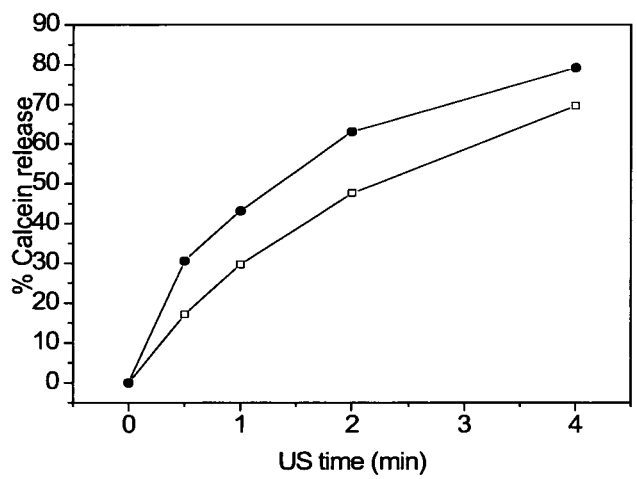
Fig. 2. Hexanol improves sonosensitivity of DSPC liposomes with cholesterol

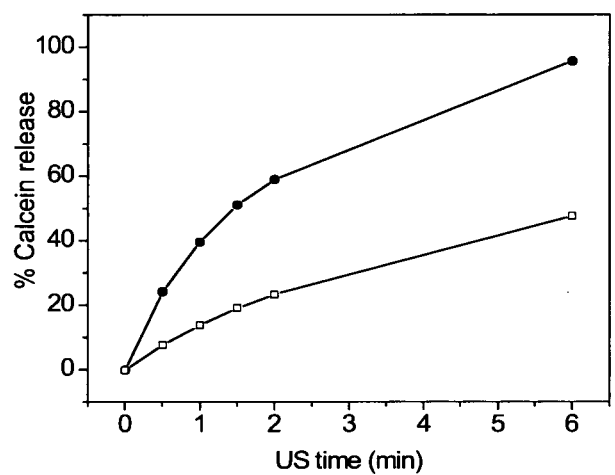
Fig. 3. Sonosensitivity of DSPE vs DSPC liposomes

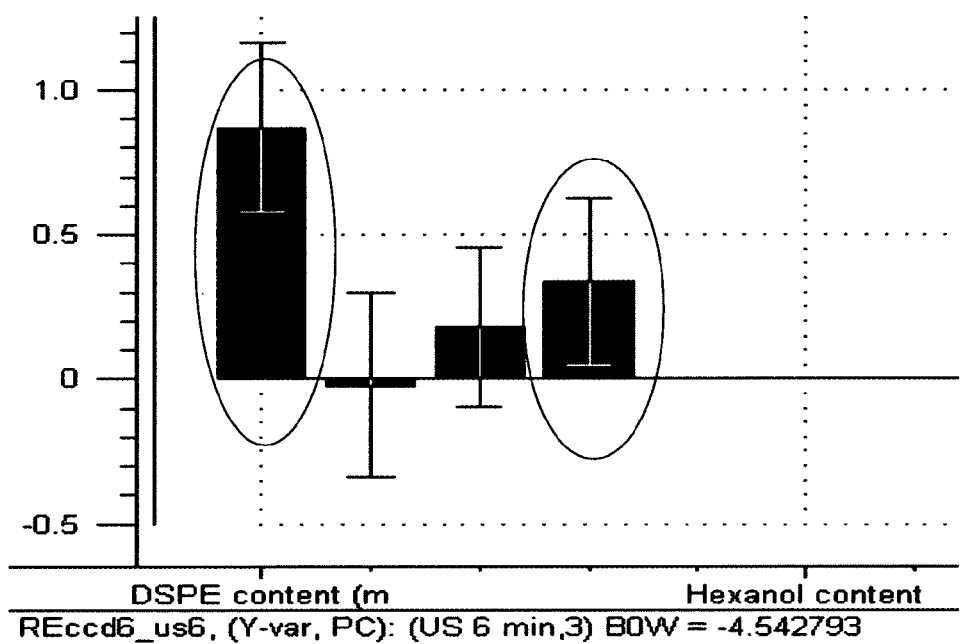
Fig. 4 Regression coefficients

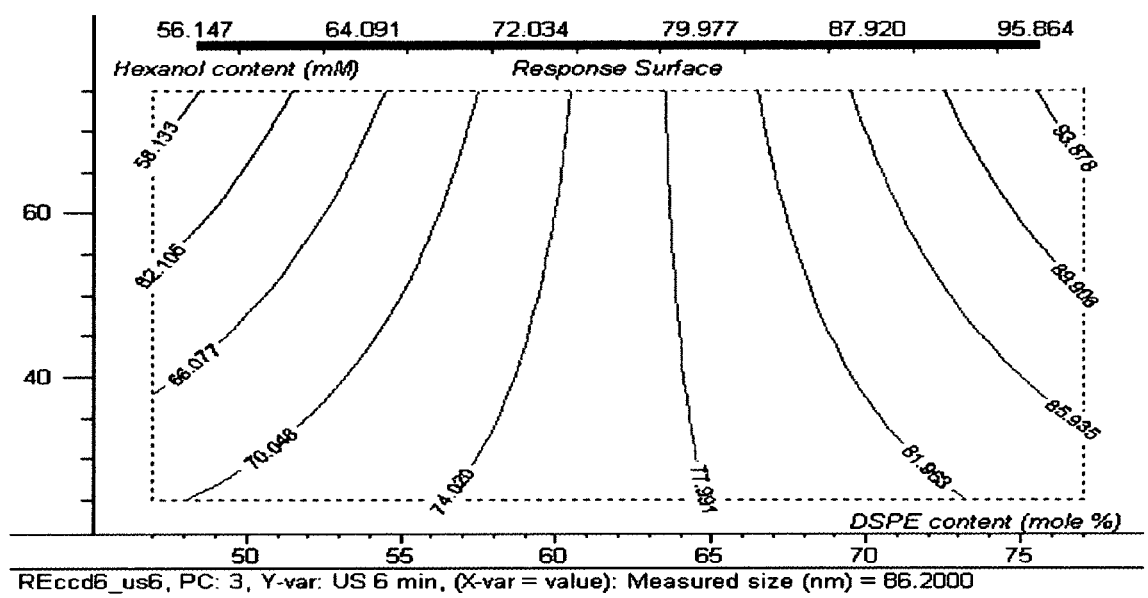
Fig. 5 Response surface

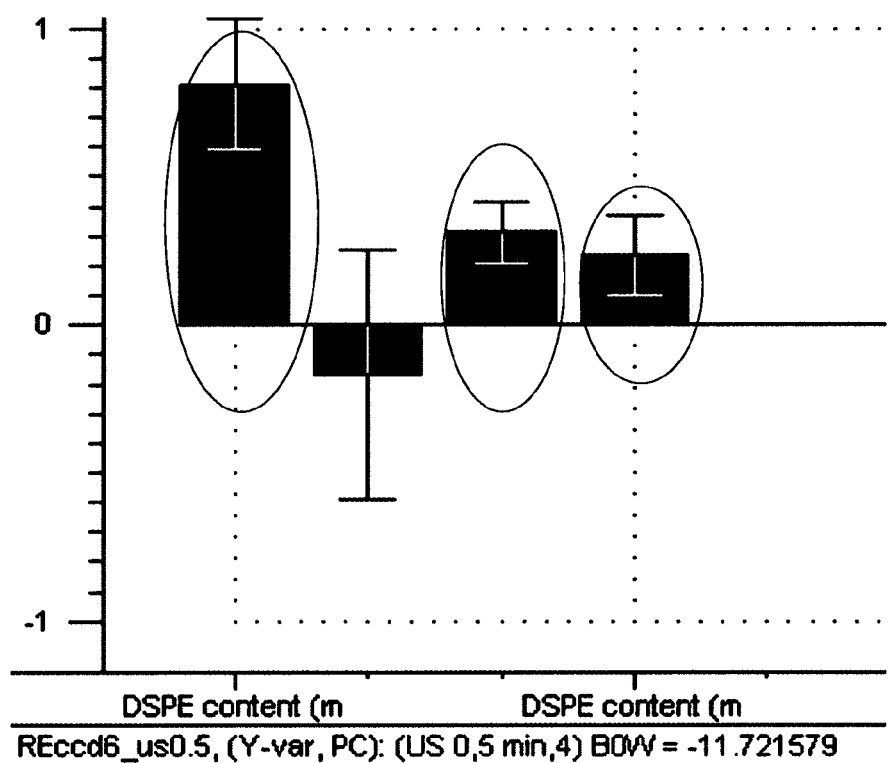
Fig. 6 Regression coefficients

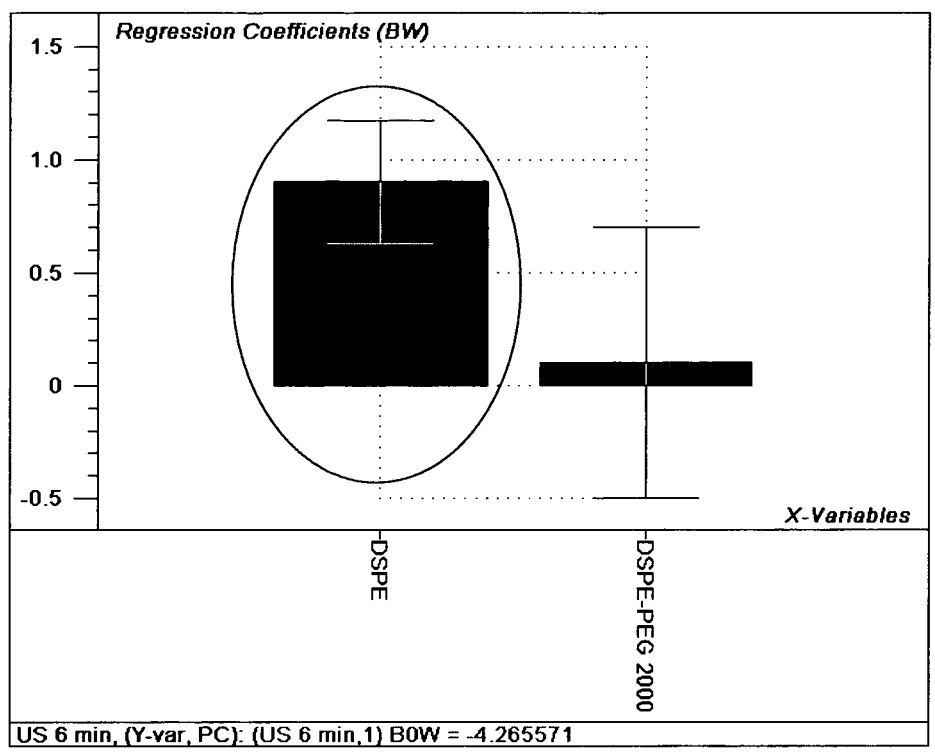
Fig. 7 Regression coefficients

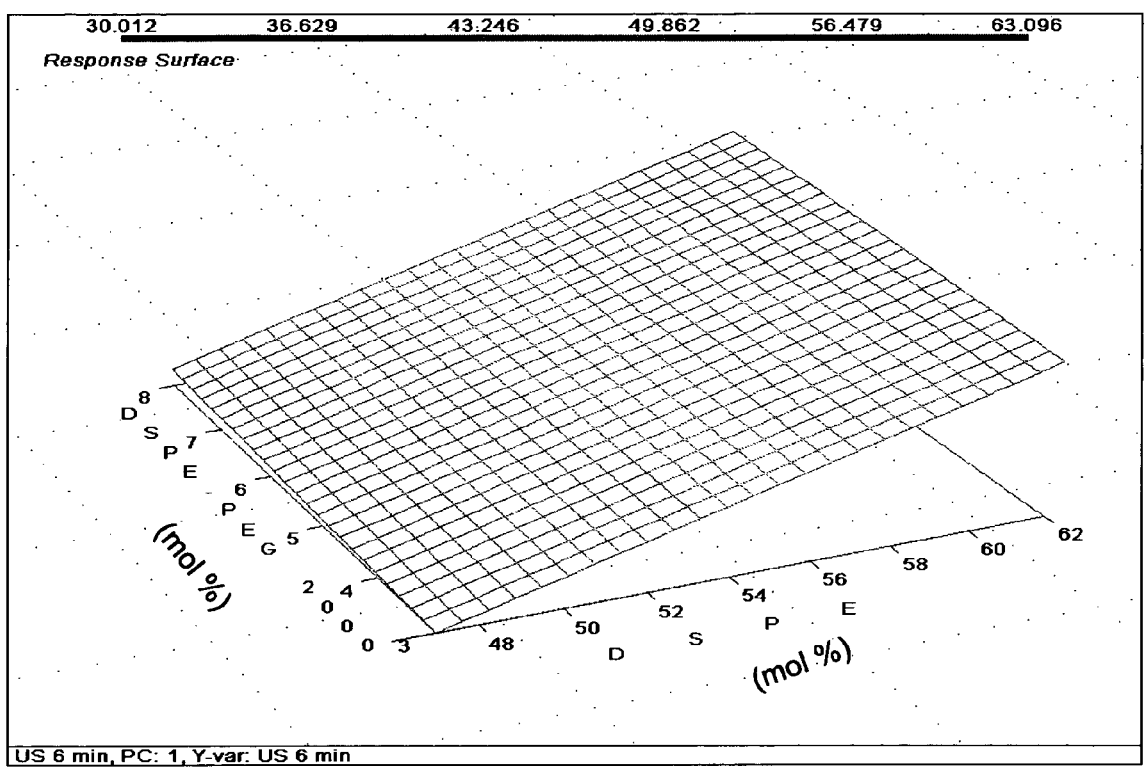
Fig. 8 Response surface

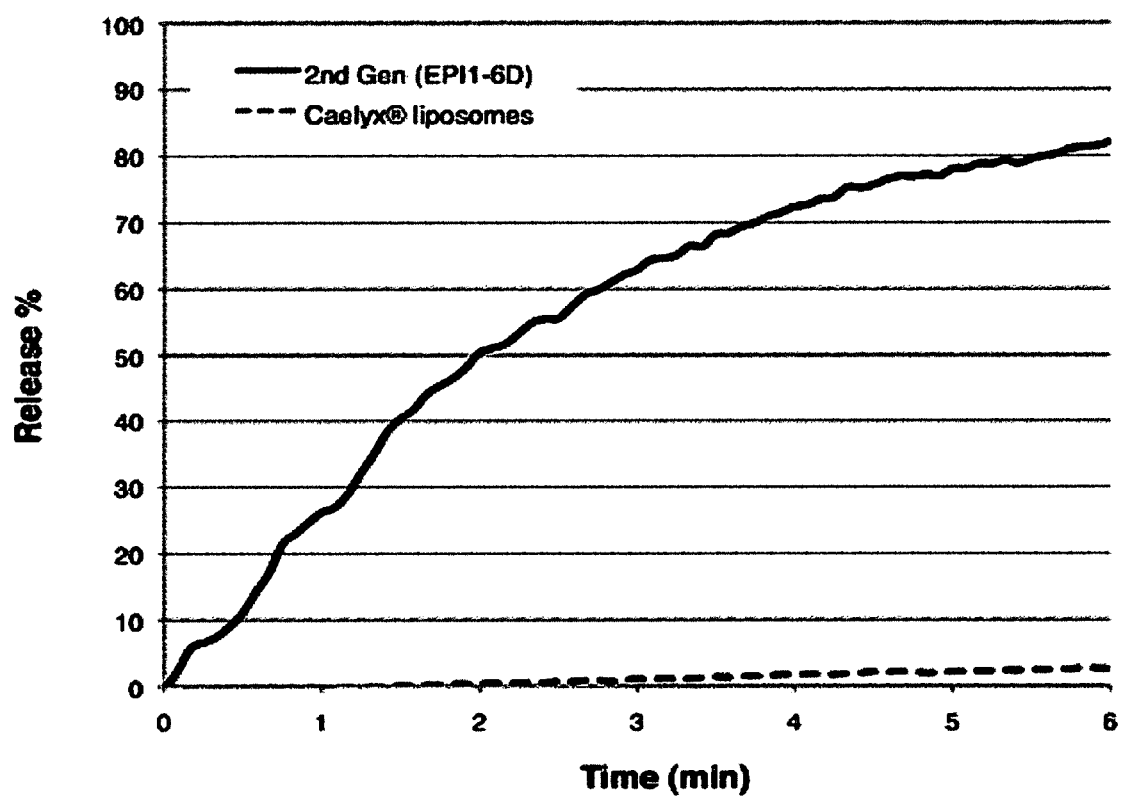
Fig. 9 US mediated drug release in 20% serum

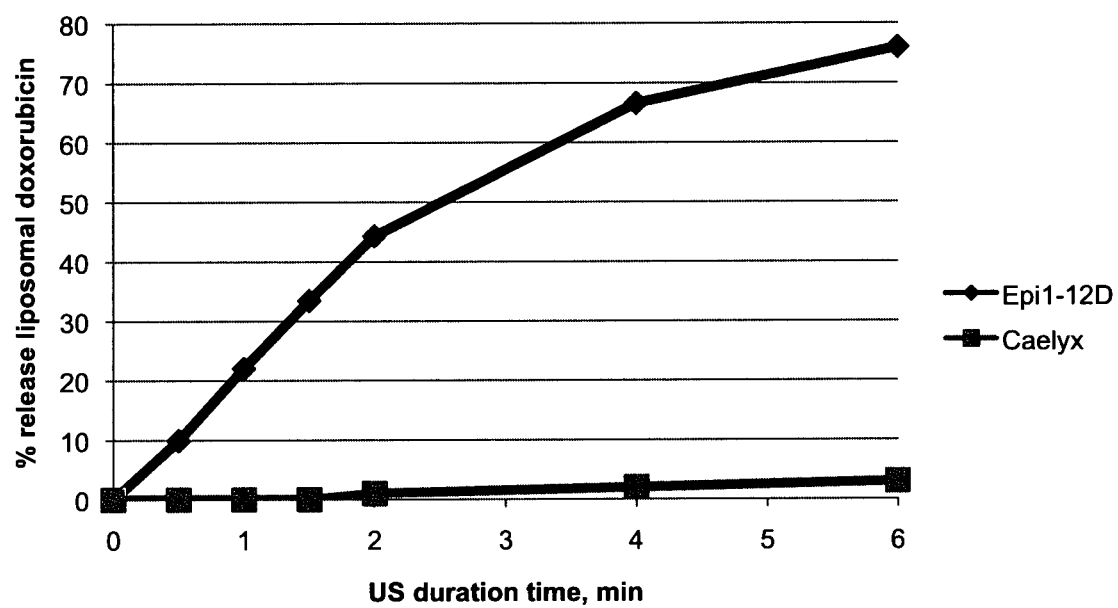
Fig. 10 US mediated release of DEPC based liposomes (epi1-12D) in comparison to Caelyx©. (20 % serum, 40 kHz).

ACOUSTICALLY SENSITIVE DRUG DELIVERY PARTICLES COMPRISING NON-LAMELLAR FORMING PHOSPHATIDYLCHOLINE

CROSS REFERENCE TO RELATED APPLICATIONS

This application is the National Phase of PCT/NO2010/000216 filed on Jun. 8, 2010, which claims priority under 35 U.S.C. 119 (e) to U.S. Provisional Application No. 61/213,443 filed on Jun. 9, 2009 and under 35 U.S.C. 119 (a) to Patent Application No. 20092195 filed in Norway on Jun. 8, 2009, all of which are hereby expressly incorporated by reference into the present application.

FIELD OF THE INVENTION

The present invention is related to particles comprising non-lamellar forming amphiphilic lipids for controlled drug delivery and release at a defined volume in an animal. Specifically, the invention relates to acoustically sensitive drug carrying particles, e.g. liposomes, as well as compositions, methods and uses thereof.

BACKGROUND OF THE INVENTION

Lack of targeted drug delivery reduces the therapeutic-to-toxicity ratio thus limiting medical therapy. This limitation is particularly evident within oncology where systemic administration of cytostatic drugs affects all dividing cells imposing dose limitations. Hence, it exists a clear need for more efficient delivery of therapeutic drugs at the disease target with negligible toxicity to healthy tissue. This challenge has to a certain extent been accommodated by encapsulating drugs in a shell protecting healthy tissue en route to the diseased volume. Such protective shells may include a number of different colloidal particles such as liposomes or other lipid dispersions, and polymer particles. However, development of such drug delivery particles has faced two opposing challenges: efficient release of the encapsulated drug at the diseased site while maintaining slow non-specific degradation or passive diffusion in healthy tissue. At present, this constitutes the main challenge in drug delivery (Drummond, Meyer et al. 1999).

Ultrasound (US) has been suggested as a method to trigger specific drug release (Pitt, Husseini et al. 2004). This may allow the engineering of robust particles protecting healthy tissue while in circulation, accumulating in the diseased volume and releasing the payload on exposure to acoustic energy. Also, US is known to increase cell permeability thus providing a twofold effect: drug carrier disruption and increased intracellular drug uptake (Larina, Evers et al. 2005; Larina, Evers et al. 2005).

Currently, four main types of US responsive particles are known: micelles, gas-filled liposomes, microbubbles and liposomes. Micelles are non-covalently self-assembled particles typically formed by molecules containing one part that is water-soluble and one that is fat soluble. The monomer aqueous solubility is typically in the mM range and at a critical concentration; micelles are formed shielding the fat soluble part from the aqueous phase. Micelle formation and disruption is therefore an equilibrium process controlled by concentration, making these particles rather unstable and less suitable for drug delivery. In addition, limited drug types can be encapsulated. Gas-filled liposomes and microbubbles are highly US responsive but too large (~1 μm) for efficient accumulation in e.g. tumour tissue. In contrast, liposomes or other lipid dispersions may encapsulate a broad range of water soluble and fat soluble drugs, as well as efficiently accumulate in e.g. tumour tissue. However, reports on ultrasound sensitive liposomes are scarce.

Lin and Thomas (Lin and Thomas 2003) report that when egg yolk liposome membranes are altered by the addition of phospholipid grafted polyethylene glycol (PEG-lipid) or non-ionic surfactants, the liposome is more responsive to US. The present applicant recently identified a synergistic interplay between liposomal PEG-lipid content and liposome size with respect to US sensitivity (NO20071688 and NO20072822, incorporated herein by reference). Here, liposomes with both high PEG-lipid content and small size showed synergistically increased US responsivity or sonosensitivity and improved drug release properties.

Long-chain alcohols may also be incorporated in phospholipid bilayers. The alcohol has one part with affinity for water (hydroxyl group) and another with affinity for oily or lipidic environments (hydrocarbon moiety). When added to a liposome dispersion some alcohol molecules remain in the aqueous phase, whilst others are incorporated in the phospholipid membrane. The extent of incorporation depends on the alcohol chain length. The longer the chain length, the more molecules will be captured within the membrane (Aagaard, Kristensen et al. 2006). The fact that organic alcohols can penetrate membranes also has an implication on local and general anaesthesia in animals (Lee 1976).

US 2005/0019266 (Unger et al) discloses lipid based vesicles comprising a lipid, targeting ligand, gas or gas precursor, and, optionally, an oil. Due to the gas bubble, such microbubbles are too large for passive in target tissues and are therefore less suited for e.g. cancer treatment.

The effect of alcohols on the liposomal membrane properties is remarkably different depending on the alcohol chain length. The membrane can be made "thinner" by inclusion of short chain alcohols (Rowe and Campion 1994; Tierney, Block et al. 2005) and the gel-to-liquid crystalline phase transition temperature of the membrane lowered by the addition of decanol (Thewalt and Cushley 1987). Interestingly, octanol which has a shorter chain is even more efficient to lower the phase transition temperature.

Phosphatidyletanolamine (PE) is the main constituent of one important class of pH sensitive liposomes (for a review see Drummond et al, Prog Lipid Res 2000; 39(5): 409-460). pH sensitive liposomes are designed to release its payload when exposed to acidic environments.

In a recent study conducted by the current applicant, it was shown for the first time that the antitumoural effect of liposomal doxorubicin (Caelyx®) could be enhanced when combined with ultrasound (Myhr and Moan 2006). However, liposomal doxorubicin (Caelyx® or Doxil®) is not engineered for ultrasound mediated drug release and shows a rather low drug release in vitro (see e.g. WO2008120998, incorporated herein in its entirety by reference).

It is herein disclosed that the sonosensitivity of drug delivery particles is surprisingly improved by the incorporation of non-lamellar forming lipids, more particularly, long-chain phosphatidylcholines The current invention may be used to efficiently deliver drugs in a defined tissue volume to combat localized diseases. Such particles may passively or actively accumulate in the target tissue and the drug payload may be dumped in the tissue by means of ultrasound thereby increasing the therapeutic-to-toxicity ratio.

Definitions
DOPE herein means 1,2-Dioleoyl-sn-Glycero-3-Phosphoethanolamine
DSPC means 1,2-distearoyl-sn-glycero-3 phosphocholine or, in short, distearoylphosphatidylcholine.
DSPE means 1,2-distearoyl-sn-glycero-3-phosphoethanolamine or distearoylphosphatidylethanolamine.
DSPE-PEGXXXX means 1,2-distearoyl-sn-glycero-3-phosphoethanolamine-N-[meth-oxy(polyethylene glycol)-XXXX, wherein XXXX signifies the molecular weight of the polyethylene glycol moiety, e.g. DSPE-PEG2000 or DSPE-PEG5000.
ISF herein mean Inverted Structure Forming.
n-alcohol means any alcohol with n carbon atoms.
PC herein means phosphatidylcholine with any composition of acyl chain.
PE means phosphatidylethanolamine with any composition of acyl chain length.
PEG means polyethylene glycol or a derivate thereof.
PEGXXXX means polyethylene glycol or a derivate thereof, wherein XXXX signifies the molecular weight of the polyethylene glycol moiety.
POPE herein means 1-palmitoyl-2-oleoyl-sn-glycero-3-phosphoethanolamine.
SOPE herein means 1-stearoyl-2-oleoyl-sn-glycero-3-phosphoethanolamine.
'US' herein means ultrasound.
'US sensitive', 'sonosensitive' or 'acoustically sensitive' herein means the ability of an entity, e.g. a particle, to release its payload upon exposure to acoustic energy.
Nominal concentration means the initial (weighed amounts per given volume) concentration of a constituent in the liposome membrane or in the hydration medium.
Inverted Structure Forming Lipid (ISF lipid) herein means an amphiphilic lipid with a spontaneous curvature of H<1, that is, with conical-like geometry.

General Provisions

The phospholipid, cholesterol, PEG-lipid and hexanol concentrations mentioned herein are nominal values unless stated otherwise.

In the current disclosure singular form means singular or plural. Hence, 'a particle' may mean one or several particles. Furthermore, all ranges mentioned herein includes the endpoints, that is, the range 'from 14 to 18' includes 14 and 18.

DETAILED DESCRIPTION OF THE INVENTION

The current inventors have found that incorporation of long-chain lipids into a particulate material enhances the sonosensitivity of said material and, thus, its capacity to release encapsulated drugs during exposure to acoustic energy.

Accordingly, the current invention relates to a particulate material comprising a long-chain lipid with, inter alia, excellent sonosensitive properties.

The particulate material may be arranged in any form of dispersion of a given internal structure. Examples of preferred structures are hexagonal structures (e.g. Hexosome®), cubic structures (e.g. Cubosomes®), emulsion, microemulsions, liquid crystalline particles and liposomes. According to a preferred embodiment, the particulate material is a membrane structure, more preferably a liposome. A liposome normally consists of a lipid bilayer with an aqueous interior.

The long-chain lipid may be any amphiphilic lipid, preferably lipids naturally prone to form so-called inverted structures. The lipid may be e.g. glycerol based (e.g. phospholipids), or a sphingolipid (e.g. ceramides).

Lipid phase behaviour can be understood in terms of molecular shape, also known as packing parameter (P) or spontaneous curvature (H). Packing parameter may be described as $$P = \frac{v}{a \cdot l}$$

where v is the volume spanned by the lipid molecule, a the area of the polar head, and l the length of the molecular (see Ole G. Mouritsen, *Life—as a matter of fat*, Springer 2005, pp. 46-51 for an introduction). Lipid molecules of P=1 will generally form lamellar bilayers, while deviations from 1 will lead to non-lamellar structures. Lipids with a parameter P<1 normally form hexagonal ($H_I$) phases or micelles, while lipids P>1 form inverted structures, like e.g. cubic, inverted hexagonal ($H_{II}$) or inverted micelles.

Without being restricted by theory, the current inventors believe that long-chain amphiphilic lipids with a packing parameter value P>1 favours sonosensitivity. Typically, amphiphilic lipids with a long acyl tail and a relatively small head have a tendency to form inverted structures. The long-chain lipid may have symmetric or asymmetric acyl chains. Preferably, at least one of the acyl chains of said lipid is 20 carbon atoms or longer, more preferably at least one of said chains is 22 carbon atoms or longer, and most preferably none of the acyl chains are shorter than 20 carbon atoms. Furthermore, at least one of the long chain lipid acyl chains is preferably unsaturated, even more preferably both acyl chains are unsaturated. Double bonds should exist in the cis conformation. In a preferred embodiment of the current invention said long chain lipid is cis-monounsaturated.

The particulate material may carry any concentration of long-chain lipid sufficient to facilitate the sonosensitive effect, although the sonosensitivity generally increase with increasing long-chain lipid content. Hence, the particulate material of the invention preferably comprises more than 10 mol %, more preferably more than 20 mol %, even more preferably more than 25 mol %, even more preferably more than 30 mol %, even more preferably more than 40 mol %, even more preferably more than 50 mol %, even more preferably more than 60 mol %, and yet even more preferably more than 70 mol % long-chain lipid.

The long-chain lipid is preferably a glycerol based amphiphilic lipid, more preferably a phospholipid, even more preferably a phosphatidylcholine (PC).

Examples of preferred symmetric and asymmetric long chain PCs are found in Table 3 and 4, respectively. More specifically, eicosenoyl, erucoyl, or nervonoyl, alone or in combination, are preferred long chain PCs.

The long chain PC may harbour additional groups on the acyl chain to make it more bulky as in e.g. diphytanoyl PC.

The current particulate material may comprise a suitable long chain PC phospholipid as the sole phospholipid or in combination with other lipids or phospholipids. Preferably, the particulate material comprises 12 mol % or more long chain PC, more preferably 25 mol % or more, even more preferably 47 mol % or more, even more preferably 52 mol % or more, even more preferably 54.5 mol % or more, even more preferably 58 mol % or more, even more preferably 62 mol % or more, even more preferably 67 mol % or more, and yet even more preferably 77 mol % or more long chain PC lipid. In general, a higher concentration of said long chain PC lipid yields higher sonosensitivity.

It is important to realise that an long chain lipid will change properties, in particular spontaneous curvature or packing parameter, if the head group is modified. Conjugation of e.g. PEG to PC may make it prone to form micelles (H>1) and it will consequently loose its capacity to form inverted structures or induce stress in the membrane during drug release.

TABLE 3

Symmetric PC

| Carbon number | Trivial | IUPAC |
| --- | --- | --- |
| 18:1 | Petroselinoyl | 6-cis-octadecenoic |
| 18:1 | Oleoyl | 9-cis-octadecenoic |
| 18:1 | Elaidoyl | 9-trans-octadecenoic |
| 18:2 | Linoleoyl | 9-cis-12-cis-octadecadienoic |
| 18:3 | Linolenoyl | 9-cis-12-cis-15-cisoctadecatrienoic |
| 20:1 | Eicosenoyl | 11-cis-eicosenoic |
| 20:4 | Arachidonoyl | 5,8,11,14(all-cis) eicosatetraenoic |
| 22:1 | Erucoyl | 13-cis-docosenoic |
| 22:6 | DHA | 4,7,10,13,16,19 (all-cis) docosahexaenoic |
| 24:1 | Nervonoyl | 15-cis-tetracosenoic |

TABLE 4

Asymmetric PC

| Carbon Number | 1-Acyl | 2-Acyl |
| --- | --- | --- |
| 18:0-18:1 | Stearoyl | Oleoyl |
| 18:0-18:2 | Stearoyl | Linoleoyl |
| 18:0-20:4 | Stearoyl | Arachidonoyl |
| 18:0-22:6 | Stearoyl | Docosahexaenoyl |

The material of the invention may further comprise an alcohol. The alcohol may be any alcohol, however, primary alcohols are preferred. The alcohol or primary alcohol may be any n-alcohol where n=2-20; preferably propanol, butanol, hexanol, heptanol, or octanol, or any combination thereof; more preferably hexanol, heptanol, or octanol, or any combination thereof. In a preferred embodiment of the current invention the alcohol or primary alcohol is hexanol. Any concentration of alcohol, e.g. hexanol, may be employed in the hydration liquid used to hydrate the lipid film and generate liposomes. In general, a higher concentration of alcohol yields higher sonosensitivity. Accordingly, the nominal alcohol concentration is at least 1 mM, preferably at least 10 mM, more preferably above 25 mM, more preferably above 50 mM, even more preferably above 60 mM, and most preferably around 75 mM. The inventors prefer that the concentration is within the range 50 mM to 80 mM, more preferably within the range 60 mM to 75 mM. In embodiments of the current application the hexanol concentration is 25, 50, 60 or 75 mM. The alcohol should be incorporated into the membrane to modulate the membrane sonosensitivity properties; in particular, the alkyl group of the alcohol should be embedded in the lipophilic part of the membrane. Thus, membranes e.g. coated with an alcohol, like polyvinyl alcohol, are not an essential part of the invention, neither are emulgating or solubilising alcohols like e.g. lanolin alcohol and octadecanol.

Sonosensitivity is not the sole parameter in selecting the optimal liposomal formulation. Other key aspects are chemical stability, blood stability, blood clearance, biodistribution, target tissue accumulation, and toxicity. The final goal is of course high therapeutic effect and/or reduced toxicity. Long chain lipids or alcohols are not alone in modulating these aspects and other components of the particle may be important in this respect.

Components for improving blood circulation time and/or further modulate sonosensitivity may be included in the material, like e.g. polyvinyl alcohols, polyethylene glycols (PEG), dextrans, or polymers. PEG or a derivate thereof, at any suitable concentration, is preferred. However, PEG concentrations are preferably up to 15 mol %, more preferably within the range 3 to 10 mol %, even more preferably in the range 3 to 8 mol %, and even more preferably within the range 5.5 to 8 mol %. In embodiments of the current invention the PEG concentration is 3, 5.5, 8, or 10 mol %. The PEG moiety may be of any molecular weight or type, however, it is preferred that the molecular weight is within the range 350 to 5000 Da, more preferably within 1000-3000 Da. In a preferred embodiment the molecular weight is 2000 Da. The PEG moiety may be associated with any molecule allowing it to form part of the particulate material. Preferably, the PEG moiety is conjugated to a sphingolipid (e.g. ceramide), a glycerol based lipid (e.g. phospholipid), or a sterol (e.g. cholesterol), more preferably to a ceramide and/or PE, and even more preferably to PE, like DMPE, DPPE, or DSPE. The acyl chain length should be the same as that of the main phospholipid of the membrane. The lipid-grafted PEG is preferably DPPE-PEG 2000 and/or DPPE-PEG 5000. In a particularly preferred embodiment lipid-grafted PEG is DSPE-PEG 2000.

To further modulate the sonosensitivity, in vitro and in vivo stability, toxicity, biological activity or any other characteristic of the particulate material of the invention, a range of other molecules may be included in the material. E.g. lipids, phospholipids, sphingolipids (e.g. ceramides), sterols, polyethyleneglycol, peptides, etc. Also, the size of the particulate material may be varied.

Accordingly, the particulate material may, in addition to the long chain lipids, further comprise a range of other lipids. Preferably, the lipid is an amphiphilic lipid such as a sphingolipid and/or a phospholipid. In a preferred embodiment the amphiphilic lipids are phospholipids of any type or source. The phospholipids may be saturated or unsaturated, or a combination thereof, although saturated phospholipids are preferred. Typically, the selected phospholipids will have an acyl chain length longer than 12 carbon atoms, more often longer than 14 carbon atoms, and even more often longer than 16 carbon atoms. Preferably the acyl chain length is within the range 14 to 24 carbon atoms, more preferably within 16 to 22 carbon atoms, even more preferably within 18 to 22. Acyl chain of different lengths may be mixed in the material of the invention or all acyl chains may have similar or identical length. In a preferred embodiment of the current invention the acyl chain length of the phospholipid is 18 carbon atoms.

Furthermore, the polar head of the phospholipid may be of any type, e.g. phosphatidylethanolamine (PE), phosphatidylcholine (PC), phosphatidic acid (PA), phosphatidyl serine (PS), or phosphatidylglycerol (PG). Consequently, the material of the invention may comprise mixtures of phospholipids with different polar heads. Neutral phospholipid components of the lipid bilayer are preferably a phosphatidylcholine, most preferably chosen from diarachidoylphosphatidylcholine (DAPC), hydrogenated egg phosphatidylcholine (HEPC), hydrogenated soya phosphatidylcholine (HSPC), distearoylphosphatidylcholine (DSPC), dipalmitoylphosphatidylcholine (DPPC) and dimyristoylphosphatidylcholine (DMPC). Negatively charged phospholipid components of the lipid bilayer may be a phosphatidylglycerol, phosphatidylserine, phosphatidylinositol, phosphatidic acid or phosphatidylethanolamine compound, preferably a phosphatidylglycerol. In a preferred embodiment of the current invention the additional or modulating phospholipid is PC, in particular DSPC. In embodiments of the current invention the DSPC concentrations are within the range 5 to 30 mol %. The level of PC may be important to modulate e.g. blood clearance rates.

The particulate material may also comprise a sterol, wherein the sterol may be cholesterol, a secosterol, or a combination thereof. The secosterol is preferably vitamin D or a derivate thereof, more particularly calcidiol or a calcidiol derivate.

The particulate material may also comprise a sterol, wherein the sterol may be cholesterol, a secosterol, or a combination thereof. The secosterol is preferably vitamin D or a derivate thereof, more particularly calcidiol or a calcidiol derivate. The particulate material may comprise any suitable sterol concentration, preferably cholesterol, depending on the specific particle properties. In general, 50 mol % sterol is considered the upper concentration limit in liposome membranes. However, the particulate material preferably comprises up to 20 mol % cholesterol, more preferably up to 30 mol %, and even more preferably up to 40 mol % cholesterol, and most preferably within the range 20 to 40 mol %. In preferred embodiments of the current invention the particulate material comprises 20, 26, 30, 35, or 40 mol % cholesterol. Accordingly, the cholesterol concentration is preferably within any of the possible ranges constituted by the mentioned embodiment concentrations. Higher concentration ranges are, however, preferred. Sterols may have a therapeutic effect, as well as improve stability and reduce blood clearance rates.

The particulate material of the invention may be of any suitable size. However, the material should preferably be less than 1000 nm, preferably less than 500 nm, more preferably less than 200 nm, more preferably 150 nm or less. In preferred embodiments the size falls within the range 50 to 200 nm, more preferably 50 to 150 nm more preferably 50 to 95 nm, even more preferably 80 to 90 nm. In one embodiment the size is around 85 nm or 85 nm. The current inventors' data show that size may be a parameter modulating the sonosensitivity of the particulate material. More specifically, size appears to be positively correlated with sonosensitivity. Hence, the optimal size range is predicted to be within the range 85 nm to 150 nm.

Furthermore, the particulate material of the invention typically comprises a drug or a functional molecule of any sort. The drug may be any drug suitable for the purpose. However, anti-bacterial drugs, anti-inflammatory drugs, anti cancer drugs, or any combination thereof are preferred. As the current technology is particularly adapted for treating cancer, anti cancer drugs are preferred. Anti cancer drugs includes any chemotherapeutic, cytostatic or radiotherapeutic drug. It may be of special interest to load the current particulate material with deoxyribonucleic acid (DNA) or ribonucleic acid (RNA), in particular small interfering RNA (siRNA).

The general groups of cytostatics are alkylating agents (L01A), anti-metabolites (L01B), plant alkaloids and terpenoids (L01C), vinca alkaloids (L01CA), podophyllotoxin (L01 CB), taxanes (L01 CD), topoisomerase inhibitors (L01CB and L01XX), antitumour antibiotics (L01D), hormonal therapy. Examples of cytostatics are daunorubicin, cisplatin, docetaxel, 5-fluorouracil, vincristine, methotrexate, cyclophosphamide and doxorubicin.

Accordingly, the drug may include alkylating agents, anti-metabolites, anti-mitotic agents, epipodophyllotoxins, antibiotics, hormones and hormone antagonists, enzymes, platinum coordination complexes, anthracenediones, substituted ureas, methylhydrazine derivatives, imidazotetrazine derivatives, cytoprotective agents, DNA topoisomerase inhibitors, biological response modifiers, retinoids, therapeutic antibodies, differentiating agents, immunomodulatory agents, and angiogenesis inhibitors.

The drug may also be alpha emitters like radium-223 (223Ra) and/or thorium-227 (227Th) or beta emitters. Other alpha emitting isotopes currently used in preclinical and clinical research include astatine-211 (211At), bismuth-213 (213Bi) and actinium-225 (225Ac).

Moreover, the drug may further comprise anti-cancer peptides, like telomerase or fragments of telomerase, like hTERT; or proteins, like monoclonal or polyclonal antibodies, scFv, tetrabodies, Vaccibodies, Troybodies, etc. Also, the material of the invention may comprise collagenases or other enzymes. In particular proteins or molecules improving the uptake and distribution of particulate material in target tissues.

More specifically, therapeutic agents that may be included in the particulate material include abarelix, aldesleukin, alemtuzumab, alitretinoin, allopurinol, altretamine, amifostine, anastrozole, arsenic trioxide, asparaginase, BCG live, bevaceizumab, bexarotene, bleomycin, bortezomib, busulfan, calusterone, camptothecin, capecitabine, carboplatin, carmustine, celecoxib, cetuximab, chlorambucil, cinacalcet, cisplatin, cladribine, cyclophosphamide, cytarabine, dacarbazine, dactinomycin, darbepoetin alfa, daunorubicin, denileukin diftitox, dexrazoxane, docetaxel, doxorubicin, dromostanolone, Elliott's B solution, epirubicin, epoetin alfa, estramustine, etoposide, exemestane, filgrastim, floxuridine, fludarabine, fluorouracil, fulvestrant, gemcitabine, gemtuzumab ozogamicin, gefitinib, goserelin, hydroxyurea, ibritumomab tiuxetan, idarubicin, ifosfamide, imatinib, interferon alfa-2a, interferon alfa-2b, irinotecan, letrozole, leucovorin, levamisole, lomustine, meclorethamine, megestrol, melphalan, mercaptopurine, mesna, methotrexate, methoxsalen, methylprednisolone, mitomycin C, mitotane, mitoxantrone, nandrolone, nofetumomab, oblimersen, oprelvekin, oxaliplatin, paclitaxel, pamidronate, pegademase, pegaspargase, pegfilgrastim, pemetrexed, pentostatin, pipobroman, plicamycin, polifeprosan, porfimer, procarbazine, quinacrine, rasburicase, rituximab, sargramostim, streptozocin, talc, tamoxifen, tarceva, temozolomide, teniposide, testolactone, thioguanine, thiotepa, topotecan, toremifene, tositumomab, trastuzumab, tretinoin, uracil mustard, valrubicin, vinblastine, vincristine, vinorelbine, zoledronate, and or an elaidic acid ester of gemcitabine, cytarabine, betamethason, prednisolon, acyclovir, ganciclovir, or ribavirin.

The drug is preferably cyclophosphamide, methotrexate, fluorouracil (5-FU); anthracyclines, like e.g. doxorubicin, epirubicin, or mitoxantrone; cisplatin, etoposide, vinblastine, mitomycin, vindesine, gemcitabine, paclitaxel, docetaxel, carboplatin, ifosfamide, estramustine, or any combination thereof; even more preferably doxorubicin, methotrexate, 5-FU, cisplatin, siRNA, an elaidic acid ester of gemcitabine, cytarabine, betamethason, prednisolon, acyclovir, ganciclovir, or ribavirin, or any combination thereof. In a preferred embodiment of the current invention the drug is a water soluble drug. In an even more preferred embodiment the drug is doxorubicin.

Furthermore, the particle of the invention may also comprise an imaging contrast agent, like e.g. an MR, X-ray, or optical imaging contrast agent, to render tracking and monitoring possible. Examples of MR and X-ray contrast agents, as well as fluorescent and bioluminescent probes may be found in the literature.

The particulate material as described anywhere supra does not comprise air bubbles of perfluorobutane or perfluoropropane gas, or any non-dissolved gasses.

Furthermore, heat sensitive or pH sensitive particles are typically not part of the current invention. More particularly, components making the particles heat sensitive, that is, releasing their payload below or above physiological temperature, like e.g. lysolipids, are typically not part of the current inventive particles. Similarly, components like cholesterolhemisuccinate (CHEMS) or fatty acids (long chain fatty acids like e.g. oleic acid (OA)), N-palmitoyl homocysteine (PHC). diplamitoyl succinyl glycerol (DSPG), or similar components making the membrane sensitive to pH below or above physiological pH are typically not part of the current invention.

In a preferred embodiment of the current invention the particulate material comprises DEPC, DSPC, cholesterol, DSPE-PEG2000 at molar percentages 52, 5, 8, 35, respectively. The size is within the range 85 to 95 nm.

Preparation of liposomes are well known within the art and a number of methods may be used to prepare the current particles.

The current invention also comprises the use of a sonosensitive particulate material comprising a long chain lipid for manufacturing a medicament for treating a condition or disease. Preferably, the particulate material is the material of the invention as described supra Another aspect of the current invention is a therapeutic method for delivering a drug to a predefined tissue volume comprising administering a particulate material comprising a long chain lipid to a patient in need thereof. More particularly, the particular material is the particle of the invention, as described supra.

Yet another aspect is a method for treating a disease or condition comprising administering a particulate material comprising a long chain lipid as defined supra to a patient in need thereof. More particularly, the particulate material is the particle of the invention, as described supra.

The use or methods further comprise the step of administering or activating said particulate material by means of acoustic energy or ultrasound. Hence, the active drug is released or administrated from the particulate material by means of acoustic energy. In this way the patient is protected against potential toxic effects of the drug en route to the target tissue and high local concentrations of the drug are obtainable in short time. Preferably, only the diseased volume is exposed to acoustic energy or ultrasound, but whole body exposures are also possible. The acoustic energy or ultrasound should preferably have a frequency below 3 MHz, more preferably below 1.5 MHz, more preferably below 1 MHz, more preferably below 0.5 MHz, more preferably below 0.25 MHz, and even more preferably below 0.1 MHz. In preferred embodiments of the current invention the frequency is 1.17 MHz, 40 kHz or 20 kHz. It should, however, be noted that focused ultrasound transducers may be driven at significantly higher frequencies than non-focused transducers and still induce efficient drug release from the current sonosensitive material. Without being limited to prevailing scientific theories, the current inventors believe that the level of ultrasound induced cavitation in the target tissue is the primary physical factor inducing drug release from the particulate material of the invention. A person skilled in the art of acoustics would know that ultrasound at any frequency may induce so-called inertial or transient cavitation.

The disease to be treated is typically of localised nature, although disseminated disease may also be treated. The disease may be neoplastic disease, cancer, inflammatory conditions, immune disorders, and/or infections, preferably localised variants. The methods described are particularly well suited to treat cancers, in particular solid tumours. Cancers readily available for ultrasound energy are preferred like e.g. cancers of head and neck, breast, cervix, kidney, liver, ovaries, prostate, skin, pancreas, as well as sarcomas. The current sonosensitive particles are well suited to treat all above conditions as they naturally accumulate in such disease volumes.

The current invention further comprises a composition comprising the above sonosensitive particulate material, as well as a pharmaceutical composition comprising the above sonosensitive particulate material.

Furthermore, the current invention comprises a kit comprising the material of the invention.

The invention also comprises a process or method of producing the sonosensitive particulate material of the invention. Said method or process comprising the steps of producing a thin film of the constituents, except membrane embedded alcohols like e.g. hexanol, of the membrane as described above, and then hydrating the film with a suitable hydration liquid. The hydration liquid may contain alcohol like e.g. hexanol. The method or process may further comprise a freeze-thaw cycle followed by an extrusion process. The drug may be included in the hydration liquid or actively loaded at the end of the process or method. Embodiments of method or process are described in detail in the Examples section.

The current invention also comprises a product produced by the process or method described supra.

BRIEF DESCRIPTION OF DRAWINGS

FIG. 1. Percent calcein release from liposomes (90 mol % DSPC, 10 mol % DSPE-PEG 2000) with (closed circles) and without hexanol (open squares) during exposure to 20 kHz ultrasound up to 4 minutes (see example 4). Hexanol containing liposomes show superior sonosensitivity.

FIG. 2. Percent calcein release from liposomes (50% mol DSPC, 10 mol % DSPE-PEG 2000, 40 mol % cholesterol) with (closed circles) and without hexanol (open squares) during exposure to 20 kHz ultrasound up to 4 minutes (see example 5). Hexanol containing liposomes show superior sonosensitivity.

FIG. 3. Percent calcein release from liposomes (3 mol % DSPE-PEG 2000, 20 mol % cholesterol, 50 mM hexanol) containing two different main phospholipids (both at 77 mol %): DSPC (open circles) and DSPE (closed squares) during exposure to 20 kHz ultrasound up to 6 minutes (see example 6). DSPE-based liposomes show superior sonosensitivity.

FIG. 4. Regression coefficients from multivariate analysis (see example 7). Statistically significant release modulators (post 6 min US) are DSPE and the DSPE*hexanol interaction (circled columns).

FIG. 5. 2D surface plot of release extent (post 6 min US) vs. DSPE and hexanol levels (see example 7). High levels of hexanol and DSPE show positive synergy, while low level of DSPE and high level of hexanol interact negatively.

FIG. 6. Regression coefficients from multivariate analysis (see example 7). Statistically significant release modulators (post 0.5 min US) are DSPE, liposome size and the DSPE*hexanol interaction (circled columns).

FIG. 7. Regression coefficients from multivariate analysis (see example 11). Statistically significant release modulator (post 6 min US) is DSPE (circled column).

FIG. 8. 3D surface plot of release extent (post 6 min US) vs. DSPE and DSPE-PEG 2000 levels (see example 11).

FIG. 9. US-mediated release of DOPE-based liposomes in 20% serum. Release curve for Caelyx® given as reference.

FIG. 10. 40 kHz ultrasound mediated drug release of DEPC based liposomes in 20% serum. Release curve for Caelyx® given as reference.

EXAMPLES

Example 1

Preparation of Liposomes Containing Fluorescent Drug Marker Calcein

DSPC, DSPE, DOPE and DSPE-PEG 2000 were purchased from Genzyme Pharmaceuticals (Liestal, Switzerland). Cholesterol, calcein, HEPES, TRITON-X100 (10% solution), sodium azide and sucrose were obtained from Sigma Aldrich. Hexanol was supplied by BDH Chemicals Ltd. (Poole, England).

Calcein carrying liposomes (liposomal calcein) of different membrane composition were prepared using the thin film hydration method (Lasic 1993). The nominal lipid concentration was 16 mg/ml. Liposomes were loaded with calcein via passive loading, the method being well known within the art. The hydration liquid consisted of 10 mM HEPES (pH 7.4) and 50 mM calcein. For the preparation of liposomal calcein containing hexanol, the hydration liquid was supplemented with a given amount of hexanol 2 days prior to usage in the lipid film hydration step.

After three freeze-thaw cycles, the liposomes were downsized to 80-90 nm by extrusion (Lipex, Biomembrane Inc. Canada) at 65° C. (DSPC liposomes), 23° C. (DOPE liposomes) and 68° C. (DSPE liposomes) through polycarbonate (Nuclepore) filters of consecutive smaller size.

Extraliposomal calcein was removed by extensive dialysis. The dialysis was performed by placing disposable dialysers (MW cut off 100 000 D) containing the liposome dispersion, in a large volume of an isosmotic sucrose solution containing 10 mM HEPES and 0.02% (w/v) sodium azide solution. The setup was protected from light and the dialysis ended until the trace of calcein in the dialysis minimum was negligible. The liposome dispersion was then, until further use, stored in the fridge protected from light.

Example 2

Characterisation of Calcein Containing Liposomes

Liposomes were characterised with respect to key physicochemical properties like particle size, pH and osmolality by use of well-established methodology.

The average particle size (intensity weighted) and size distribution were determined by photon correlation spectroscopy (PCS) at a scattering angle of 173° and 25 deg C. (Nanosizer, Malvern Instruments, Malvern, UK). The width of the size distribution is defined by the polydispersity index. Prior to sample measurements the instruments was tested by running a latex standard (60 nm). For the PCS measurements, 10 µL of liposome dispersion was diluted with 2 mL sterile filtered isosmotic sucrose solution containing 10 mM HEPES (pH 7.4) and 0.02% (w/v) sodium azide. Duplicates were analysed.

Osmolality was determined on non-diluted liposome dispersions by freezing point depression analysis (Fiske 210 Osmometer, Advanced Instruments, MA, US). Prior to sample measurements, a reference sample with an osmolality of 290 mosmol/kg was measured; if not within specifications, a three step calibration was performed. Duplicates of liposome samples were analysed.

Example 3

US Mediated Release Methodology and Quantification for Calcein Containing Liposomes Liposome samples were exposed to 20 or 40 kHz ultrasound up to 6 min in a custom built sample chamber as disclosed in Huang and MacDonald (Huang and Macdonald 2004). The US power supply and converter system was one of two systems: (1) 'Vibra-Cell' ultrasonic processor, VC 750, 20 kHz unit with a 6.35 cm diameter transducer or (2) 'Vibra-Cell' ultrasonic processor, VC754, 40 kHz unit with a 19 mm cup horn probe, both purchased from Sonics and Materials, Inc. (USA). Pressure measurements were conducted with a Bruel and Kjaer hydrophone type 8103.

Both systems were run at the lowest possible amplitude, i.e. 20 to 21% of maximum amplitude. For the 20 kHz system this translates to a transducer input power of 0.9-1.2 W/cm$^2$ and a peak-to-peak transducer pressure of about 460 kPa.

For the US measurements, liposome dispersions were diluted in a 1:500 volume ratio, with isosmotic sucrose solution containing 10 mM HEPES (pH 7.4) and 0.02% (w/v) sodium azide. Duplicates were analysed.

The release assessment of calcein is based on the following well-established methodology: Intact liposomes containing calcein will display low fluorescence intensity due to self-quenching caused by the high intraliposomal concentration of calcein (here 50 mM). Ultrasound mediated release of calcein into the extraliposomal phase can be detected by an increase in fluorescence intensity due to a reduced overall quenching effect. The following equation is used for release quantification:

$$\% \text{ release} = \frac{(F_u - F_b)}{(F_T - F_b)} \times 100$$

Where $F_b$ and $F_u$ are, respectively, the fluorescence intensities of the liposomal calcein sample before and after ultrasound application. $F_T$ is the fluorescence intensity of the liposomal calcein sample after solubilisation with the surfactant (to mimic 100% release). Studies have shown that for calcein containing liposomes the solubilisation step must be performed at high temperature, above the phase transition temperature of the phospholipid mixture.

Fluorescence measurements were either carried out with a Luminescence spectrometer model LS50B (Perkin Elmer, Norwalk, Conn.) equipped with a photomultiplier tube R3896 (Hamamatsu, Japan) or a QE6500 spectrometer with scientific grade detector (Ocean Optics B.V., Duiven, The Netherlands). Fluorescence measurements are well known to a person skilled in the art.

Example 4

Hexanol Improves the Sonosensitivity of Liposomes

Two liposome formulations, composed of 90 mol % DSPC and 10 mol % DSPE-PEG 2000, and containing either hexanol or not were prepared, according to Example 1. For the liposomes containing hexanol, the calcein solution (hydration liquid) was doped with hexanol at 60 mM concentration. The size of the hexanol containing liposomes was measured to 82 nm, while non-hexanol containing liposomes measured 95 nm (see Example 2 for size measurement methodology). The liposomes (diluted 1:500 v/v) were exposed to 20 kHz in the US chamber and the percentage of calcein release was estimated by fluorescence measurements after 0.5, 1, 2 and 4 minutes of ultrasound treatment (see Example 3 for US release and quantification methodology). FIG. 1 shows that for the liposome formulation containing hexanol (full dots), the sonosensitivity was improved giving an increase in calcein release of 20% (in absolute value) compared to the liposome formulation containing no hexanol (open squares) this after 4 minutes of ultrasound treatment.

Example 5

Hexanol Improves the Sonosensitivity of Cholesterol Containing Liposomes

The development of a stable liposome formulation often requires the inclusion of a sterol in the membrane. Also, liposome size is known to affect ultrasound sensitivity. Therefore, the effect of incorporating hexanol on the sonosensitivity was evaluated for similar sized liposomes consisting of 50 mol % DSPC, 10 mol % DSPE-PEG2000 and 40 mol % cholesterol. The liposomes were loaded with calcein as previously described and the size of hexanol and non-hexanol containing liposomes was measured to 88 nm and 89 nm, respectively. For the preparation of liposomes containing hexanol, the calcein solution (hydration liquid) was doped with hexanol at 60 mM concentration.

The ultrasound experiment was executed as described above at 20 kHz. Results are shown in FIG. 2. An increase in calcein release of at least 15% (in absolute value) was observed for hexanol containing liposomes (closed circles) compared to liposomes devoid of hexanol (open squares). The beneficial effect of hexanol was seen already after 0.5 min US.

We conclude that that the inclusion of hexanol in the liposome dispersion comprising cholesterol increases the sonosensitivity and drug release properties.

Example 6

PE Improves Sonosensitivity of Liposomes

To evaluate the effect of PE on liposomal formulations containing hexanol, liposomes composed of either 77 mol % DSPC or 77 mol % DSPE were investigated. Both formulations further consisted of 20 mol % cholesterol and 3 mol % DSPE-PEG 2000. The calcein solution (hydration liquid) contained 50 mM hexanol. The size of the DSPC-based and DSPE-based liposomes was 80 and 84 nm, respectively. The ultrasound experiment was performed at 20 kHz and the percentage of calcein release was estimated by fluorescence measurements after 0.5, 1, 1.5, 2 and 6 minutes of ultrasound exposure.

FIG. 3 shows that for the DSPE-based liposomes (full dots), the sonosensitivity was increased compared to DSPC-based liposomes (open squares).

We conclude that the inclusion of PE increases the sonosensitivity and drug release properties of liposomes.

Example 7

PE and Hexanol Synergistically Improve Sonosensitivity of Liposomes

As disclosed above the liposome sensitivity vis-à-vis US is affected by the inclusion of hexanol and/or PE lipids. To further investigate the effect of alcohols and/or PE lipids on liposomal sonosensitivity a multivariate study design was conducted. The initial study design comprised 11 different formulations where the amount of DSPE and hexanol was varied at different levels (see Table 5). For all formulations the level of cholesterol and DSPE-PEG 2000 was kept constant at 20 and 3 mol %, respectively.

Liposomes were prepared and analysed as previously described. Release experiments were performed at 40 kHz ultrasound. Results from the study are listed in Table 6.

TABLE 5

Multivariate PE/hexanol design

| Exp | Hexanol (mM) | DSPE (mol %) | DSPC (mol %) | DSPE-PEG 2000 (mol %) | Cholesterol (mol %) |
|---|---|---|---|---|---|
| 1 | 25 | 47 | 30 | 3 | 20 |
| 2 | 25 | 77 | 0 | 3 | 20 |
| 3 | 75 | 47 | 30 | 3 | 20 |
| 4 | 75 | 77 | 0 | 3 | 20 |
| 5 | 50 | 62 | 15 | 3 | 20 |
| 6 | 50 | 62 | 15 | 3 | 20 |
| 7 | 25 | 62 | 15 | 3 | 20 |
| 8 | 50 | 47 | 30 | 3 | 20 |
| 9 | 50 | 77 | 0 | 3 | 20 |
| 10 | 75 | 62 | 15 | 3 | 20 |
| 11 | 50 | 62 | 30 | 3 | 20 |

TABLE 6

Batch data

| Exp | DSPE content (mole %) | Hexanol content (mM) | Measured size (nm) | US 0.5 min (%) | US 1 min (%) | US 1.5 min (%) | US 2 min (%) | US 6 min (%) |
|---|---|---|---|---|---|---|---|---|
| 1 | 47 | 25 | 86 | 15.8 | 27.0 | 35.4 | 41.6 | 69.1 |
| 2 | 77 | 25 | 84 | 21.3 | 33.3 | 43.0 | 52.2 | 83.1 |
| 3 | 47 | 75 | 84 | 7.9 | 14.3 | 20.2 | 25.0 | 53.7 |
| 4 | 77 | 75 | 86 | 24.1 | 39.3 | 50.8 | 61.9 | 96.8 |
| 5 | 62 | 50 | 86 | 10.0 | 17.8 | 24.6 | 30.6 | 61.1 |
| 6 | 62 | 50 | 86 | 15.5 | 28.0 | 36.8 | 44.5 | 76.7 |
| 7 | 62 | 25 | 87 | 18.9 | 31.4 | 39.1 | 46.9 | 78.3 |
| 8 | 47 | 50 | 86 | 10.7 | 18.3 | 24.7 | 30.9 | 62.1 |
| 9 | 77 | 50 | 88 | 23.2 | 38.2 | 48.9 | 56.6 | 87.7 |
| 10 | 62 | 75 | 92 | 20.6 | 34.5 | 45.5 | 53.0 | 82.5 |
| 11 | 62 | 50 | 83 | 13.5 | 24.8 | 33.8 | 41.2 | 73.3 |

Multivariate analysis of the data in Table 6 showed that DSPE was the main release modulator; the higher the DSPE level the higher the release extent as evidenced by a statistically significant positive regression coefficient (FIG. 4). Optimum sonosensitivity was achieved when DSPE and hexanol were combined at high levels. Thus, a statistically significant interaction effect between DSPE and hexanol was observed (FIGS. 4 and 5). Liposome size also contributed positively to sonosensitivity. The size effect was statistically significant at short US durations; the larger the size the higher the release extent (FIG. 6).

Example 8

PE Improves Sonosensitivity of Liposomes

The study in Example 7 was extended to include DSPE liposome formulations containing no hexanol. DSPE-PEG 2000 and cholesterol levels were held constant at 3 mol % and 20 mol %, respectively, whilst the target size was 85 nm. DSPC functioned as additional phospholipid. Liposomes were prepared and tested at 40 kHz ultrasound. Release data are listed in Table 7.

TABLE 7

Batch data

| Exp | DSPE content (mole %) | Hexanol content (mM) | Measured size (nm) | US 0.5 min (%) | US 1 min (%) | US 1.5 min (%) | US 2 min (%) | US 6 min (%) |
|---|---|---|---|---|---|---|---|---|
| 13 | 47 | 0 | 85 | 5.1 | 9.1 | 12.6 | 15.5 | 34.2 |
| 14 | 62 | 0 | 87 | 17.2 | 29.6 | 38.0 | 43.7 | 64.5 |

Multivariate analysis of the data in Table 6 and 7 again confirmed that DSPE was a significant contributor to sonosensitivity.

Example 9

High Levels of PEG do not Reduce Sonosensitivity of DSPE Liposomes

In a further extension of Examples 7 and 8, the DSPE-PEG 2000 level was increased from 3 to 8 mol %. Cholesterol was kept at 20 mol %, while DSPC functioned as additional phospholipid. Release data (at 40 kHz) are listed in Table 8.

TABLE 8

Batch data

| Exp | DSPE content (mole %) | Hexanol content (mM) | Measured size (nm) | US 0.5 min (%) | US 1 min (%) | US 1.5 min (%) | US 2 min (%) | US 6 min (%) |
|---|---|---|---|---|---|---|---|---|
| 15 | 62 | 50 | 83 | 25.5 | 43.3 | 55.7 | 64.6 | 91.0 |
| 16 | 62 | 0 | 84 | 20.3 | 31.6 | 40.9 | 47.6 | 75.3 |

Example 10

DOPE Improves Sonosensitivity of Liposomes

Two liposomal calcein formulations containing DOPE as the main lipid were investigated. DSPE-PEG 2000 and cholesterol levels were kept constant at 8 mol % and 20 mol %, respectively. DSPC functioned as additional phospholipid. Release data (at 40 kHz) are given in Table 9.

TABLE 9

Batch data

| Exp | DOPE content (mole %) | DSPC content (mole %) | Measured size (nm) | US 0.5 min (%) | US 1 min (%) | US 1.5 min (%) | US 2 min (%) | US 6 min (%) |
|---|---|---|---|---|---|---|---|---|
| 1 | 72 | 0 | 89 | 21 | 38 | 51 | 80 | 91 |
| 2 | 62 | 10 | 69 | 21 | 36 | 48 | 78 | 92 |

The data shows that DOPE-based liposomes have good sonosensitivity in the absence of any alcohols. For a given cholesterol, DSPE-PEG 2000 and PE level, DOPE liposomes have a higher sonosensitivity compared to DSPE-based liposomes (Exp 2 vs. Exp 16).

Example 11

Effect of DSPE-PEG 2000 and Cholesterol Level on Sonosensitbity of DOPE-based Liposomes To further investigate the effect of cholesterol and DSPE-PEG 2000 on liposomal sonosensitivity a multivariate study design was conducted. The study design comprised 11 different formulations where the amount of DOPE, cholesterol and DSPE-PEG 2000 was varied at different levels (see Table 10).

TABLE 10

Multivariate design

| EXP | DOPE content (mole %) | DSPC content (mole %) | DSPE-PEG 2000 content (mole %) | Cholesterol content (mole %) |
|---|---|---|---|---|
| 1C | 52 | 5 | 8 | 35 |
| 2C | 52 | 20 | 8 | 20 |
| 3C | 52 | 10 | 3 | 35 |
| 4C | 72 | 5 | 3 | 20 |
| 5C | 52 | 20 | 3 | 25 |
| 6C | 57 | 20 | 3 | 20 |
| 7C | 67 | 5 | 8 | 20 |
| 8C | 57 | 5 | 3 | 35 |
| a | 58 | 11 | 5 | 26 |
| b | 58 | 11 | 5 | 26 |
| 9a | 58 | 11 | 5 | 26 |

Liposomes were prepared and analysed as previously described. Release experiments were performed at 40 kHz ultrasound. Results from the study are listed in Table 11.

TABLE 11

Batch data

| EXP | Mean size (nm) | US 0.5 min | US 1 min | US 1.5 min | US 2 min |
|---|---|---|---|---|---|
| 1C | 84 | 30.6 | 55.3 | 70.1 | 82.2 |
| 2C | 81 | 31.9 | 56.8 | 78.0 | 92.9 |
| 3C | 85 | 28.0 | 54.0 | 70.8 | 83.8 |
| 4C | 83 | 24.3 | 46.3 | 61.8 | 72.6 |
| 5C | 86 | 27.7 | 50.2 | 65.0 | 73.8 |
| 6C | 89 | 22.6 | 41.0 | 55.1 | 66.2 |
| 7C | 84 | 22.7 | 43.8 | 58.9 | 69.9 |

TABLE 11-continued

Batch data

| EXP | Mean size (nm) | US 0.5 min | US 1 min | US 1.5 min | US 2 min |
|---|---|---|---|---|---|
| 8C | 83 | 25.5 | 45.6 | 60.7 | 71.6 |
| a | 77 | 19.6 | 48.7 | 69.2 | 85.1 |
| b | 81 | 22.8 | 43.9 | 59.0 | 69.3 |
| 9a | 87 | 25.3 | 46.1 | 60.2 | 71.4 |

The results show that variations in cholesterol and DSPE-PEG 2000 levels do not markedly affect the sonosensitivity of DOPE-based liposomes.

Example 12

Preparation and Characterisation of Doxorubicin-containing Liposomes

DSPC, DSPE, DOPE and DSPE-PEG 2000 were purchased from Genzyme Pharmaceuticals (Liestal, Switzerland). Doxorubicin HCl was obtained from Nycomed, Norway. Cholesterol, citrate tri-sodium salt, Triton X-100 (10% solution), HEPES, ammonium sulphate, sodium azide, and sucrose were obtained from Sigma Aldrich. Hexanol was supplied by BDH Chemicals Ltd. (Poole. England).

Liposomes of different membrane composition were prepared using the thin film hydration method (Lasic 1993). The dry lipid film was hydrated with either 300 mM ammonium sulphate (pH 5.5 unbuffered) or 300 mM citrate (pH 4), see Table 12. The nominal lipid concentration was 20 mg/ml after hydration. In liposomes containing hexanol, the hydration solution was doped with a given amount of hexanol.

After hydration the liposome preparations were submitted to 3 freeze thaw cycles in a dry ice/acetone/methanol mixture. The liposomes were downsized to small unilamellar vesicles of 80-90 nm by stepwise extrusion (Lipex. Biomembrane Inc. Canada) through polycarbonate (Nuclepore) filters. During extrusion the temperature was kept constant around the transition temperature for the respective liposome formulations.

Formation of an ammonium sulphate gradient or a pH citrate gradient was obtained by extensive dialysis. The dialysis was performed by placing disposable dialysers (MW cut off 100 000 D) containing the liposome dispersion. Three consecutive dialysis exchanges against a large volume of either an isotonic sucrose solution (pH 5.5 unbuffered) or an isotonic 20 mM HEPES buffered NaCl solution (pH 7.4) (Table 12).

The liposome dispersions were then mixed with a given volume of doxorubicin HCl solution to give a final drug to lipid ratio of 1:8 or 1:16 and a final nominal lipid concentration of 16 mg/ml. After ½-1 h incubation at 23-75° C. (dependent on the membrane composition) the liposome sample was cooled down to room temperature. The percent drug loading was determined by fluorescence measurements after separating free drug by dialysis or by using Sephadex G-50 columns. After loading the extraliposomal phase was exchanged with an isotonic 10 mM HEPES buffered sucrose solution (pH 7.4) or 20 mM HEPES buffered NaCl solution (pH 7.4) (Table 12).

TABLE 12

Solutions and their concentrations used for remote loading of doxorubicin liposomes.

| Active loading procedure | Composition of hydration buffer | Hydration buffer mOsm/kg | Composition of solution for gradient dialysis | Gradient solution mOsm/kg | Composition of external buffer (after loading) | External buffer mOsm/kg |
|---|---|---|---|---|---|---|
| Ammonium sulphate gradient | 300 mM ammonium sulphate (pH 5.5) | 650 | 255 mM sucrose (pH 5.5 unbuffered) | 290 | 10 mM HEPES/ 255 mM sucrose (pH 7.4) | 300 |
| Citrate gradient | 300 mM citrate - trisodium salt (pH 4.0) | 1500 | 20 mM HEPES/150 mM NaCl (pH 7.4) | 290 | 20 mM HEPES/ 150 mM NaCl (pH 7.4) | 300 |

US measurements and release quantification were performed as described in Example 3 except for the following modification; the solubilisation step was performed at ambient temperature.

Physicochemical and release data for various doxorubicin containing liposome formulations are summarised in Table 13 and 14. Multivariate analysis of the various EPI 2D liposome formulations (Table 13) confirmed that DSPE was the main contributor to sonosensitivity. The positive regression coefficient implying that increased DSPE level increases the release extent (FIG. 7). FIG. 8 shows the response surface plots for release extent (post 6 min US) vs. DSPE and DSPE-PEG 2000 levels.

Release data for DOPE-based doxorubicin containing liposomes (Table 14) correspond to data obtained for calcein—liposomes of identical lipid composition and size (Table 9). The very high sonosensitivity of these DOPE based formulations is presumed to be related to the strong non-lamellar characteristics of the DOPE lipid, which upon ultrasound exposure induce release of liposomal drug.

TABLE 13

Batch data

| Exp No | DSPE:DSPC:DSPE-PEG2000:chol Mole ratio % | Dox. conc. loading (mg/ml) | % Encapsulation | Size (nm) | Release value (%) min US 0.5 | 1 | 1.5 | 2 | 4 | 6 |
|---|---|---|---|---|---|---|---|---|---|---|
| SS1 | 62:15:3:20 | 2.0 | 87 | 93 | 6 | 14 | 20 | 26 | 42 | 51 |
| SS2 | 47:5:8:40 | 2.0 | 94 | 85 | 4 | 8 | 12 | 16 | 28 | 34 |
| 20SS | 62:2.5:5.5:30 | 2.0 | 96 | 85 | 4 | 9 | 14 | 18 | 34 | 43 |
| Hx20SS* | 62:2.5:5.5:30 | 2.0 | 100 | 84 | 6 | 14 | 20 | 24 | 38 | 45 |
| 28SS | 54.5:10:5.5:30 | 2.0 | 78 | 88 | 5 | 10 | 14 | 17 | 27 | 32 |
| 26SS | 47:15:8:40 | 2.0 | 100 | 92 | 2 | 5 | 9 | 11 | 21 | 28 |
| 29SS | 54.5:7.5:8:30 | 2.0 | 71 | 84 | 7 | 14 | 22 | 26 | 43 | 53 |
| 30SS | 47:15:8:30 | 2.0 | 73 | 80 | 8 | 17 | 23 | 30 | 50 | 64 |
| 28 b.up | 54.5:10:5.5:30 | 1.0 | 94 | 84 | 2 | 4 | 6 | 9 | 15 | 21 |
|  |  |  |  |  | 2 | 5 | 8 | 10 | 20 | 25 |
| 26 Lyon | 47:5:8:40 | 1.0 | 93 | 82 | 3 | 3 | 6 | 7 | 14 | 17 |
|  |  |  |  |  | 2 | 4 | 6 | 8 | 15 | 20 |
| 26#1 PoP | 47:5:8:40 | 1.0 | 87 | 89 | 5 | 9 | 14 | 19 | 30 | 32 |
| 26#2 PoP | 47:5:8:40 | 1.0 | 99 | 81 | 3 | 5 | 6 | 9 | 17 | 25 |
| 26#3 PoP | 47:5:8:40 | 1.0 | 98 | 83 | 4 | 7 | 11 | 12 | 22 | 25 |
| Epi2-1D | 47:5:3:20 | 1.0 | 97 | 83 | 8 | 14 | 18 | 21 | 29 | 34 |
| Epi2-2D | 62:15:3:20 | 1.0 | 100 | 86 | 12 | 21 | 28 | 32 | 47 | 60 |
| Epi2-3D | 62:10:8:20 | 1.0 | 99 | 84 | 13 | 20 | 27 | 37 | 53 | 68 |
| Epi2-4D | 47:25:8:20 | 1.0 | 97 | 89 | 5 | 9 | 11 | 15 | 25 | 34 |
| Epi2-5D | 54.5:20:5.5:20 | 1.0 | 97 | 88 | 6 | 10 | 14 | 17 | 30 | 37 |
| Epi2-6D | 54.5:20:5.5:20 | 1.0 | 97 | 85 | 10 | 18 | 24 | 47 | 38 | 45 |
| Epi1-28citrate | 54.5:10:5.5:30 | 1.0 | 100 | 95 | 5 | 8 | 12 | 16 | 26 | 32 |
| Epi2-7D | 62:5:3:30 | 1.0 | 100 | 87 | 9 | 19 | 26 | 31 | 49 | 60 |
| Epi2-8D | 62:0:8:30 | 1.0 | 97 | 87 | 14 | 28 | 39 | 46 | 62 | 74 |

*Containing hexanol in the internal phase
US studies performed at 40 kHz and 20-21% amplitude; 1:500 or 1:250 (bold) dilution is used

TABLE 14

Batch data

| Exp No | DOPE:DSPC:DSPE-PEG2000:chol Mole ratio % | Dox. conc. loading (mg/ml) | % Encapsulation | Size (nm) | Release value (%) min US 0.5 | 1 | 1.5 | 2 | 4 | 6 |
|---|---|---|---|---|---|---|---|---|---|---|
| Epi1-6D | 62:10:8:20 | 1.0 | 56 | 88 | 20 | 35 | 46 | 61 | 90 | 100 |

Example 12

Stability and Sonosensitivity of DOPE-based Liposomes in Serum

DOPE-liposomes (Table 14) show very good stability in 20% serum (1:125 dilution); no leakage of doxorubicin could be detected after 6 hours incubation at 37 deg C.

The sonosensitivity of DOPE-based liposomes (1:500 dilution) is also unaltered in 20% serum (at 40 kHz) and is markedly superior to the commercial liposomal doxorubicin product (Caelyx®). See FIG. 9.

Example 13

Sonosensitive Liposomes Comprising Long Chain Unsaturated PC Erucoyl Show High Sonosensitivity DEPC (Erucoyl or 13-cis-docosenoic) is a long chain PC phospholipid with an acyl chain length of 22 carbon atoms and with one unsaturated bond. Liposomes with composition DEPC:DSPC:DSPE-PEG2000:CHOL of molar percentage 52:5:8:35 were produced and doxorubicin loaded as described above. The formulation showed no leakage after 6 hours of incubation in 20% serum at 37° C. In ultrasound experiments almost 80% of the drug load was released after 6 minutes of 40 kHz ultrasound exposure in 20% serum (see FIG. 10). The experiment was conducted as described supra. As can be seen from FIG. 10 there is a dramatic difference between the ultrasound sensitivity of the DEPC formulation and commercial liposomal product Caelyx®. The latter product consists mainly of saturated PC phospholipids DPPC and DSPC.

Example 14

Liposomes Comprising Long Chain PC Show Improved Sonosensitivity

TABLE 15

| Mol % X:Y:DSPC: DSPE-PEG2000:chol | X | Y | SIZE, nm (P.I) | 40 kHz US 20% serum | | | | | | Serum leakage 6 h/37° C. |
|---|---|---|---|---|---|---|---|---|---|---|
| | | | | 0.5 | 1 | 1.5 | 2 | 4 | 6 | |
| 52:0:5:8:35 | DNPC | | 86.7 (0.082) | 5.7 | 11.9 | 15.9 | 21.1 | 39.7 | 54.9 | −1 |
| 25:27:0:8:40 | DNPC | DBPC | 87.0 (0.091) | 3.4 | 8.7 | 15.1 | 22.0 | 44.3 | 57.5 | −2 |
| 25:0:27:8:40 | | DOPC | 87.8 (0.070) | 3.1 | 6.3 | 9.0 | 12.2 | 25.9 | 35.7 | −1 |

Table 15 shows characterisation data, including sonosensitivity, for several long chain PC based liposomes. Liposomes based on 1,2-dinervonoyl-sn-glycero-3-phosphocholine (DNPC, Nervonoyl or 15-cis-tetracosenoic; comprising acyl chain length of 24 carbon atoms with one unsaturated bond). Liposomes with composition DNPC:DSPC:DSPE-PEG2000:CHOL of mol % 52:5:8:35 were produced and doxorubicin loaded as described supra. The formulation showed only 1% leakage after 6 hours of incubation in 20% serum at 37° C. In ultrasound experiments 84.0% and 54.9% of the drug load was released after 6 minutes of 40 kHz ultrasound exposure in HEPES buffered sucrose solution and 20% serum, respectively. The experiment was conducted as described supra. The DNPC based sonosensitive liposomes are almost 6 times more sonosensitive compared to benchmark PC based liposomes (Caelyx©, based on hydrogenated soy PC, i.e. mainly DPPC and DSPC).

In a another study the above DNPC liposomes were reformulated to also comprise 1,2-dibehenoyl-sn-glycero-3-phosphocholine (DBPC), DBPC is a saturated long chain PC with an acyl chain length of 22 carbon atoms, with the composition DNPC:DBPC:DSPE-PEG2000:CHOL of molar percentage 25:27:8.40. The formulation was loaded successfully with doxorubicin as described supra and tested with respect to serum stability and sonosensitivity: the formulation showed only 2% leakage after 6 hours of incubation in 20% serum at 37° C., while 83.0% and 57.5% of the drug load was released after 6 minutes of 40 kHz ultrasound exposure in HEPES buffered sucrose solution and 20% serum, respectively.

Example 15

Liposomes Comprising Low Concentrations of Long Chain Unsaturated PC Show Improved Sonosensitivity Liposomes with composition DEPC:DSPC:DSPE-PEG2000:CHOL of molar percentage 25:27:8:40 were manufactured and doxorubicin loaded as described above. In ultrasound experiments almost 18% of the drug load was released after 6 minutes of 40 kHz ultrasound exposure in HEPES buffered sucrose, while the equivalent release in 20% serum was 13%. The experiment was conducted as described supra. As can be seen from FIG. 10 the release from hydrogenated soy PC based liposomes (Caelyx®) is only 3% after 6 min ultrasound exposure in 20% serum.

Example 15

Animal Blood Clearance Kinetics

For anaesthesia a mixture of 2.4 mg/ml tiletamine/2.4 mg/ml zolazepam (Zoletil® vet, Virbac Laboratories, Carros, France), 3.8 mg/ml xylazine (Narcoxyl® vet, Roche, Basel, Switzerland) and 0.1 mg/ml butorphanol (Torbugesic®, Fort Dodge Laboratories, Fort Dodge, Iowa) was administered at a dose of 0.1 ml s.c. Healthy mice received 7 mg/kg liposomal doxorubicin (DXR) under anaesthesia as a single i.v. bolus through the tail vein. At different post injection time points animals were sacrificed in groups (n=4). The total blood volume was collected by cardiac puncture using heparinized syringes and stored in heparinized tubes. The samples were kept on ice bath until storage at −80° C.

Example 16

Quantification of DXR in Blood

Quantification of DXR was done as described by Gabizon et al. 1989. In brief, 0.1 ml whole blood samples (lysed due to freezing), was mixed with 1.9 ml 50% acidified ethanol (equal parts of distilled water and conc. ethanol), creating a 1:20 dilution. Duplicate samples were prepared. Tissue samples were added acidified ethanol in a 1:10 dilution and homogenized using a Polytron® Benchtop Homogenizer. The samples were incubated for 24 hrs at 4° C. in the dark. Following incubation the precipitate was removed by centrifugation (20000 g, 20 min, 4° C.) and the supernatant (containing extracted DXR) stored at −20° C. until fluorescence measurements. The extracted DXR was quantified by fluorescence measurements at excitation wavelength 470 nm and measured intensity at emission wavelength 590 nm. A standard curve was produced by adding known amounts of liposomal DXR (Caelyx®, Schering-Plough) to blood and homogenized tissues and incubated and centrifuged as described above.

Example 17

Long Chain Lipids Improve Blood Clearance Kinetics of Liposomes

Healthy mice received DEPC based liposomal doxorubicin as described in Example 15. Blood clearance was analysed as described in Examples 15 and 16. At 24 hrs 20% of injected dose was still in circulation.

References

Aagaard. T. M. kristensen. et al. (2006). "Packing properties of 1-alkanols and alkanes in a phospholipid membrane." *Biophys. Chem.* 119: 61-68.

Andresen. T. L. S. S. Jensen. et al. (2005). "Advanced Startegies in Liposomal Cancer Therapy: problems and prospects of active and tumor specific drug release." *Prog. Lipid Res.* 44(1): 68-97.

Drummond. D. C. O. Meyer. et al. (1999). "Optimizing Liposomes for Delivery of Chemotheraoeutic Agents to Solid Tumors." *Pharmacol. Rev.* 51(4): 691-743.

Holland. J. W. P. R. Cullis. et al. (1996). "Poly(ethylene glycol)-Lipid Conjugates Promote Bilayer Formation in Mixtures of Non-Bilayer-Forming Lipids." *Biochemistry* 35: 2610-2617.

Huang. S, and R. C. Macdonald (2004). "Acoustically active liposomes for drug encapsulation and ultrasound-triggered release." *Biochim. Biophys. Acta* 1665: 134-141.

Larina. I. V. B. M. Evers. et al. (2005). "Enhancement of drug delivery in tumors by using interaction of nanoparticles with ultrasound radiation." *Technol Cancer Res Treat* 4(2): 217-226.

Larina. I. V. B. M. Evers. et al. (2005). "Optimal drug and gene delivery in cancer cells by ultrasound-induced cavitation." *Anticancer Res* 25(1A): 149-156.

Lasic. D. D. (1993). *Liposomes from Physics to Applications*. Amsterdam. Amsterdam Elsevier Science Publishers BV.

Lee. A. G. (1976). "Interactions between anesthetics and lipid mixtures. Normal alcohols." *Biochemistry* 15: 2448-2454.

Lin. H. Y. and J. L. Thomas (2003). "PEG-Lipids and Oligo (ethylene glycol) Surfactants Enhance the Ultrasonic Permeabilizability of Liposomes." *Langmuir* 19(4): 1098-1105.

Myhr. G. and J. Moan (2006). "Synergistic and tumor selective effects of chemotherapy and ultrasound treatment." *Cancer Lett.* 232: 206-213.

Pitt. W. G. G. A. Husseini. et al. (2004). "Ultrasonic drug delivery—a general review."*Expert Opin Drug Deliv* 1(1): 37-56.

Rowe. E. S, and J. M. Campion (1994). "Alcohol Induction of Interdigitation in Distearoylphosphatidylcholine: Fluorescence Studies of Alcohol Chain Length Requirements." *Biophys. J.* 67: 1888-1895.

Thewalt. J. L. and R. J. Cushley (1987). "Phospholipid/cholesterol membranes containing n-alkanols: a 2H-NMR study." *Biochim. Biophys. Acta* 905: 329-338.

Tierney. K. J. D. E. Block. et al. (2005). "Elasticity and Phase Behavior of DPPC Membrane Modulated by Cholesterol. Ergosterol. and Ethanol." *Biophys. J.* 89: 2481-2493.

We claim:

1. A sonosensitive liposome having a packing parameter of P>1, comprising
   at least 25 mol % of a phosphatidylcholine (PC) comprising an unsaturated acyl chain of at least 20 carbon atoms or longer,
   wherein said liposome comprises no air bubbles or undissolved gases.

2. The liposome of claim 1, wherein the acyl chain is at least 22 carbon atoms or longer.

3. The liposome of claim 1, wherein the phospholipid comprises two unsaturated acyl chains.

4. The liposome of claim 1 not comprising cholesterol-hemisuccinate, free fatty acids and/or lysolipids.

5. The liposome of claim 1, wherein the PC is eicosenoyl, erucoyl (DEPC), and/or nervonoyl.

6. The liposome of claim 1, wherein the phospholipid is DEPC.

7. The liposome of claim 1, wherein said liposome comprises at least 50 mol % of a PC comprising an unsaturated acyl chain of at least 20 carbon atoms or longer.

8. The liposome of claim 1, further comprising a polyethyleneglycol (PEG) or a derivative thereof.

9. The liposome of claim 1 comprising 8 mol % PEG or more.

10. The liposome of claim 1, further comprising cholesterol.

11. The liposome of claim 1, further comprising 20 mol % or more cholesterol.

12. The liposome of claim 1, wherein said liposome has a size less than 500 nm.

13. The liposome of claim 1, wherein said liposome has a size within the range 50 to 150 nm.

14. The liposome of claim 1, further comprising a drug.

15. The liposome of claim 1, wherein said liposome comprises DEPC:disteraoylphosphatidylcholine (DSPC):Cholesterol: distearoylphosphatidylethanolamine-PEG (DSPE-PEG) at mole percentages 52:5:8:35.

16. A method for treating a condition or disease, comprising
   administering a sonosensitive liposome having a packing parameter of P>1, comprising a phosphatidylcholine (PC) of at least 20 carbon atoms or longer, comprising no air bubbles or nondissolved gases, to a patient in need thereof, wherein said liposome is activated or released by acoustic energy.

17. The method of claim 16, wherein said patient suffers from cancer, an immune disorder, an infection, or an inflammatory disease.

18. A pharmaceutical composition comprising the liposome of claim 1.

19. The liposome of claim 14, wherein the drug is doxorubicin, an elaidic acid ester of cytarabine, aldesleukin, filgrastim, pegfilgrastim, or sargramostim.

* * * * *